US005981710A

United States Patent [19]

Hai et al.

[11] Patent Number: 5,981,710

[45] Date of Patent: Nov. 9, 1999

[54] THERAPEUTIC HEMOGLOBIN COMPOSITION HAVING ISOTROPICALLY INCREASED SIZE

[75] Inventors: Ton That Hai, Mundelein; David E. Pereira, Crystal Lake; Deanna J. Nelson, Libertyville, all of Ill.

[73] Assignee: Baxter International, Inc., Deerfield, Ill.

[21] Appl. No.: 08/896,743

[22] Filed: Jul. 21, 1997

[51] Int. Cl.[6] .............................. A61K 35/14; C07G 3/00; A01N 43/04

[52] U.S. Cl. ......................... 530/385; 530/402; 525/54.1; 525/54.2; 536/4.1; 536/18.5; 536/18.6; 536/123; 536/123.1; 536/123.13; 536/126; 514/23; 514/25; 514/54; 514/55

[58] Field of Search .................................... 530/385, 402; 424/193.1, 194.1; 525/54.1, 54.2; 536/4.1, 18.5, 18.6, 123, 123.1, 123.13, 126; 514/23, 25, 54, 55

[56] References Cited

U.S. PATENT DOCUMENTS

| | | | |
|---|---|---|---|
| 4,613,665 | 9/1986 | Larm | 536/20 |
| 4,698,387 | 10/1987 | Schmidt et al. | 525/54.1 |
| 4,900,816 | 2/1990 | Wong | 536/120 |
| 4,943,630 | 7/1990 | Jacquinet et al. | 536/123 |
| 5,079,337 | 1/1992 | Leonard et al. | 530/385 |
| 5,110,909 | 5/1992 | Dellacherie et al. | 530/385 |
| 5,248,766 | 9/1993 | Nelson et al. | 530/385 |
| 5,510,418 | 4/1996 | Rhee et al. | 525/54.2 |
| 5,527,893 | 6/1996 | Burns et al. | 514/53 |
| 5,605,938 | 2/1997 | Roufu et al. | 514/59 |

FOREIGN PATENT DOCUMENTS

WO 96/34889 11/1996 WIPO .

OTHER PUBLICATIONS

Hascall et al., Immunology of Chondroitin/Dermatan Sulfate, in Glycoimmunology, Alavi, A. and Axford, A. S. eds., Plenum Press, New York, pp. 205–216 (1995)–published sufficiently before filing such that the month is not an issue.

Connective Tissue Proteoglycans, in The Biochemistry of Glycoproteins and Proteogycans, W. J. Lennarz ed., Plenum Press, New York, pp. 286–314 (1980).

*Primary Examiner*—Cecilia J. Tsang
*Assistant Examiner*—Abdel A. Mohamed
*Attorney, Agent, or Firm*—Senniger, Powers, Leavitt & Roedel

[57] ABSTRACT

Novel polysaccharide compounds are disclosed for decorating biomolecular surfaces to increase isotropic size and mask antigenicity. The oligosaccharides may be synthesized as repeating disaccharide units, or may be derived by acid hydrolysis of naturally occurring polysaccharides. Such natural sources include chondroitins obtained from shark cartilage, or hyaluronic acid. The polyanionic sulfate groups contained in the sugar moieties impart negative charges which repel the molecules from the negatively charged wall of capillaries, to lengthen retention times of decorated drug molecules, such as crosslinked hemoglobin, in the peripheral circulation.

9 Claims, 11 Drawing Sheets

1. Linker No. 1

2. Linker No. 2

3. Branched Linker

Tosyl ester

Tresyl ester

Halide

Maleimide

Epoxide

Halide

THERAPEUTIC HEMOGLOBIN COMPOSITION HAVING ISOTROPICALLY INCREASED SIZE

CROSS REFERENCE TO RELATED APPLICATION

This application hereby incorporates by reference the complete text of application Ser. No. 08/897,336, entitled "REAGENTS FOR ISOTROPIC SIZE ENHANCEMENT", by inventors Ton That Hai, David E. Pereira and Deanna J. Nelson, filed on the same date as this application, Jul. 21, 1997.

FIELD OF THE INVENTION

This invention relates to hemoglobin compositions and other biopolymer substrates having isotropically increased size and isotropically distributed negative charge. The invention also relates to such isotropically modified hemoglobin compositions having oxygen binding affinity, viscosity and colloid osmotic pressure in therapeutically useful ranges.

BACKGROUND OF THE INVENTION

All vertebrate hemoglobins have the same molecular configuration. Hemoglobin is a protein made up of four polypeptide subunits, two alpha chains and two non-alpha chains. A natural cavity is defined by certain amino acids in each subunit. This cavity contains a heme prosthetic group, consisting of a porphyrin ring and an iron ion. Hemoglobin in the form capable of reversibly binding and releasing oxygen, the iron ion is in the +2 oxidation state, i.e., the ferrous form, and is sequestered by each porphyrin ring within the protein. In a hemoglobin tetramer, each alpha subunit is associated with a non-alpha subunit to form two stable alpha/non-alpha dimers, which in turn associate to form the tetramer. The subunits are noncovalently associated through Van der Waal's forces, hydrogen bonds and salt bridges. The molecular weight of native human hemoglobin is about 65,000 Daltons.

Hemoglobin can be collected from mammalian blood or derived from genetically engineered sources. However, even after stringent purification, unmodified vertebrate hemoglobin has no therapeutic utility. Free hemoglobin has an affinity for oxygen too high for release of oxygen to the tissues. Further, unmodified free vertebrate hemoglobin readily dissociates into alpha/non-alpha dimers in the circulation. High concentrations of these dimers overwhelm the haptoglobin scavenging system and accumulate in the tubules of the kidney, where they are nephrotoxic. Chemical modification of hemoglobin is necessary to overcome these deficiencies.

The tetrameric structure of hemoglobin may be stabilized by intramolecular covalent crosslinking between at least two of the subunits of the native hemoglobin. The molecular weight of the resulting hemoglobin composition is about 65,000 Daltons, similar to that of the source hemoglobin. Moreover, the manner of intramolecular crosslinking may be selected to provide both stabilization of the tetrameric structure of hemoglobin and a change in hemoglobin conformation sufficient to impart oxygen binding characteristics similar to those in freshly collected red blood cells. For example, native hemoglobin may be extracted from red blood cells, purified, and intramolecularly crosslinked. Examples of crosslinked hemoglobins and methods for their preparation are described in U.S. Pat. Nos. 4,001,401 and 4,053,590, which disclose intramolecular crosslinking between an alpha and beta subunit of a hemoglobin tetramer utilizing compounds such as halogenated cycloalkanes, diepoxides, and diazobenzidines. WO 90/13309 (Staat der Nederlanden de Minister Van Defeuric) discloses a method for crosslinking hemoglobin through a beta-beta subunit linkage. In the present method, a preferred modified hemoglobin is crosslinked with bis(3,5-dibromosalicyl) fumarate to create a fumarate crosslink between the two alpha subunits. This crosslinked hemoglobin is more fully described, together with methods for its preparation, in U.S. Pat. Nos. 4,598,064, 4,600,531, RE 34,271, omitting the chromatography step. It is preferably manufactured under the conditions disclosed in U.S. Pat. No. 5,128,452 (Hai) to prevent crosslinking between the beta chains. The preferred diaspirin crosslinked hemoglobin will hereafter be referred to as "DCLHb". U.S. Pat. Nos. 4,598,064, 4,600,531, RE 34,271, and 5,128,452 are hereby incorporated by reference. In addition, the genes encoding subunits of a desired naturally occurring or mutant hemoglobin can be cloned, placed in a suitable expression vector and inserted into an organism, animal, or plant, or into cultured animal or plant calls or tissues. The hemoglobin produced therefrom can be expressed and collected as described, for example, in Hoffman, S. J. and Nagai, K. in U.S. Pat. No. 5,028,588. Transgenic animals can be produced that express non-endogenous hemoglobin (Logan, J. S. et al., PCT application WO 92/22646).

These intramolecularly crosslinked hemoglobin compositions have therapeutic utility both for humans and other mammals. See, for example, Sloan, Koenigsberg, and Bickell, "The Use of Diaspirin Cross-linked Hemoglobin (DCLHb) in the Hospital Management of Hemorrhagic Hypovolemic Shock", *Academic Emerg Med* 1995; 2(5): Abstract No. 78.

Hemoglobin compositions having a molecular weight of about 65,000 Daltons have a short half-life in the circulatory system, because they are able to traverse cellular pores in the membrane of the blood vessels and capillaries, entering the interstitial spaces between endothelial cells lining the lumen. Consequently, these hemoglobin compositions are lost from the circulation while they still retain therapeutic utility. The hemoglobin composition diaspirin crosslinked hemoglobin (DCLHb), which has a molecular weight of about 65,000 Daltons, has an elimination half-life of 2.5 hours for a 25- and 50-mg/kg dose and an elimination half-life of 3.3 hours for a 100 mg/kg dose. (Przybelski, et al., *Crit Care Med* 1996; 24(No. 12): 1993–2000.)

Further chemical modifications to hemoglobin which increase molecular weight have been used in attempts to extend the duration of circulation of the hemoglobin composition. See Bunn, H. F., *Amer J Hematol* 42:112–117, 1993. These additional modifications include conjugation and polymerization. In addition, modification to increase overall negative charge may also extend half-life in the circulation, since the negative charges in the vessel walls tends to repel hemoglobin with high negative charge.

Conjugated hemoglobin is hemoglobin to which a non-protein macromolecule is bound covalently. The properties of hemoglobins conjugated to polysaccharides have been reviewed by Dellacherie. (E. Dellacherie, "Polysaccharides in Oxygen-carrier Blood Substitutes", chapter 17 in *Polysaccharides in Medicinal Applications,* S. Dumitriu, ed. Marcel Dekker, Inc., New York, 1996, pages 525–545.) For example, hemoglobin may be conjugated to inulin in a process disclosed in U.S. Pat. No. 4,377,512 (Ajinomoto). Hemoglobin may be conjugated to a polysaccharide such as dextran in a process disclosed in U.S. Pat. No. 4,900,816 (Fisons). Macromolecular conjugates of hemoglobin and a substituted dextran, together with a process for its preparation, are provided in U.S. Pat. Nos. 5,079,337 and 5,110,909 (Merieux). A further example of a conjugated hemoglobin composition is a hemoglobin chemically modified by polyalkylene glycol, which is described together with a process for its preparation in WO 91/07190 (Enzon). An example of a hemoglobin conjugated to poly(alkylene oxide) and a process for its preparation are provided in U.S. Pat. Nos. 4,301,144, 4,412,989, and 4,670,417, and in Japanese Patent Nos. 59-104323 and 61-053223 (Ajinomoto).

A polymerized hemoglobin is one in which intermolecular crosslinking of hemoglobin tetrameres has been used to increase the molecular weight of the modified hemoglobin. An example of a polymerized hemoglobin and a process for its preparation are described in U.S. Pat. No. 4,777,244 which discloses a method for crosslinking and polymerizing with aliphatic dialdehydes.

A hemoglobin, modified by a combination of methods, is exemplified by the following. Hemoglobins modified by pyridoxal-5'-phosphate to adjust the oxygen affinity and by polyethylene glycol conjugation and processes for its preparation are described in Japanese Patent Nos. 59-089629, 59-103322 and 59-104323 (Ajinomoto). U.S. Pat. No. 5,248,766 discloses a crosslinking polymerizing strategy and a process for covalently interconnecting intramolecularly crosslinked tetrameric units with oxiranes to form polyhemoglobins with molecular weights in excess of 120, 000 Daltons.

Even though conjugation and polymerization both increase the molecular weight of the constituent hemoglobin, these hemoglobin do not have isotropically increased size. This is illustrated in the ball and stick structures of FIG. 1. The process of polymerization with a bifunctional reagent such as glutaraldehyde generates a homologous series of hemoglobin polymers having, for the most part, linear structures analogous to barbells or beads on a string FIGS. 1*a* and 1*b*. Since the polymers comprise multiple hemoglobin units, the molecular weight of each of the component polymers is about (64,500)×n, where n has a value from 2 to 10 or more. If one considers the functional diameter of the polymeric hemoglobin stretched lengthwise along an arbitrary x-axis, it is larger than that of a single hemoglobin. However, if one considers the functional diameter of the polymeric hemoglobin from the perspective of either terminus (i.e., along the z-axis) as in FIG. 1*c*), this diameter is no greater than that of a single hemoglobin molecule. Therefore, the polymeric hemoglobins can still readily leak out of capillaries through the pores of the luminal membranes and interstitial junctions, thereby shortening the period of therapeutic effectiveness. Similarly, conjugation with a polysaccharide such as dextran or inulin generates a conjugated hemoglobin having a linear structure analogous to the barbell structure in FIG. 1*a*. Thus, conjugates of this type also are characterized by a functional diameter no greater than that of a single hemoglobin molecule.

Other problems arise in conventionally conjugated hemoglobin. Conjugation of hemoglobin with a polyalkylene oxide, such as polyethylene glycol (PEG) or polyoxyethylene, or polymerization of hemoglobin undesirably increases its viscosity (Winslow, R. M., "The Design of Blood Substitute Oxygen Carriers for Clinical Applications", In: *Shock: From Molecular and Cellular Level to Whole Body,* K. Okada et al., editors. Elsevier Science, 1996, pages 323–333). Viscous fluids are difficult to administer, and would unacceptably alter the fluid properties of the blood.

A hemoglobin uniformly greater in diameter than the diameters of the cellular pores would be retained for longer periods of time in the circulatory system, particularly if the surface modification also isotropically dispersed negative surface charge would be repulsed from the surface of endothelial cells lining the lumen of the circulatory system. See Rennke, Cotran, Venkatachalam, *J Cell Biol* 67:638, 1975. No known hemoglobin composition meets these criteria.

SUMMARY OF THE INVENTION

It is an object of this invention to provide a hemoglobin composition having isotropically increased size and having isotropically dispersed negative surface charge. It is a further object of the invention to provide a hemoglobin composition having an unexpectedly low viscosity relative to its increased size.

Pharmaceutical formulations of the invention can be prepared for both clinical medicine and veterinary use. These formulations can be useful for, for example, subcutaneous, intravenous, intraperitoneal, or intramuscular injection, or topical or oral administration in small or large volumes. Said formulations of the invention can be administered by any conventional means such as by oral or aerosol administration, by transdermal, transmembrane or mucus membrane absorption, or by infusion.

In one embodiment, the compositions can be formulated pharmaceutically for use in therapeutic applications in clinical or veterinary medicine. For example, the formulations of the present invention can be used in compositions useful for the replenishment of the systemic circulating volume of fluid in a mammal, for the restoration of the systemic circulation in a mammal, for the restoration of oxygen delivery, and for the replenishment of the oxygen delivery capacity.

The compositions of the present invention can be formulated pharmaceutically for use for the replenishment of the systemic circulating volume of fluid in a mammal following hemorrhage, i.e., as volume expanders. These compositions provide both additional fluid volume and oncotic pressure due to the presence of the large hemoglobin protein molecule.

Such compositions formulated in a pharmaceutically compatible carrier fluid are useful as red blood cell replacement fluids and can be used for the treatment of hemorrhage and hypovolemic shock where blood volume is lost and both fluid volume and oxygen carrying capacity must be replaced. These compositions can also be used for replacement of blood lost during surgical procedures or where the patient's blood is removed and saved for reinfusion at the end of surgery or during recovery (i.e., acute normovolemic hemodilution or hemoaugmentation).

In a further embodiment, the formulation of the instant invention can be used to treat anemia, both by providing additional oxygen carry capacity in a patient that is suffering from anemia and by stimulating and supporting hematopoiesis.

In accordance with the present invention, oligosaccharide-biopolymer conjugates are provided for either masking biologically reactive sites or for isotropic size enhancement, the oligosaccharide moiety having the structure according to formula I:

$$B'\text{-}(A\text{-}B)_n\text{-}A'\text{-}NH\text{-}L\text{-}Y$$

wherein A and B are sugars which may be of N-acetylgalactosamine, N-acetylglucosamine, glucuronic acid, iduronic acid or glucose forming a repeating disaccharide unit in which A and B are joined covalently by a glycosidic bond between C-1 of sugar A and C-3 or C-4 of sugar B. The A-B disaccharide units are joined covalently to form an oligosaccharide by a glycosidic bond between C-1 of penultimate sugar B of a first disaccharide unit and C-3 or C-4 of sugar A in the next successive disaccharide unit. B' is a sugar at the non-reducing terminus of the oligosaccharide of ring structure identical to sugar B, and A' is a 1-amino, 1-amido, or 1-imino acyclic hexose joined covalently by a glycosidic bond between C-1 of sugar B at the terminus opposite the non-reducing terminus of said oligosaccharide and C-3 or C-4 of sugar A'. This structure is further joined covalently by a 1-amino, 1-amido, or 1-imino linkage to linker L comprising an aliphatic, acyclic carbon chain containing one or more moieties, which can be an ether, thio ether, or amide. The linker bridges sugar A' and one or more groups Y, which may be a methylene radical, β-hydroethylene radical, carboxyl radical, succinamide alpha radical, or nullity. These Y groups are the portions of the Z group described in copending patent application Ser. No. 08/897,336, remaining after reaction with the nucleophilic groups contained in the biopolymer. As used herein, the term "nullity" means the absence of any portion of the Z group which is lost as a leaving group upon reaction of the electrophilic group with the nucleophilic group of the biopolymer. The biopolymer, which may be a protein, carbohydrate, or polynucleotide is thereby covalently attached to the linker L.

DETAILED DESCRIPTION OF THE PREFERRED EMBODIMENTS

Figure 7A:
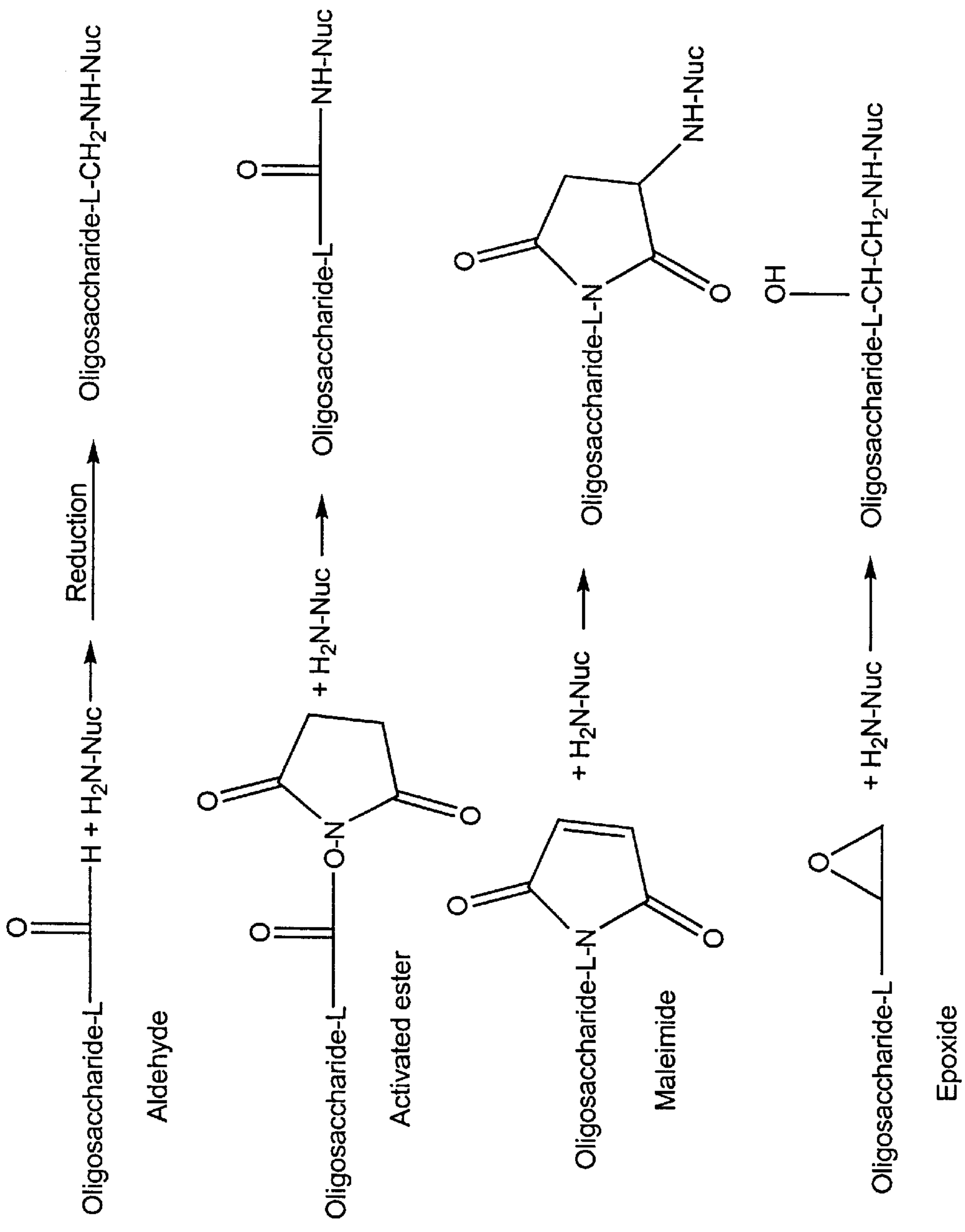
FIG. 7 gives the molecular structures for a number of possible Z groups useful in the disclosed compound, reagents prior to conjugation with a biopolymer.
Figure 7B:
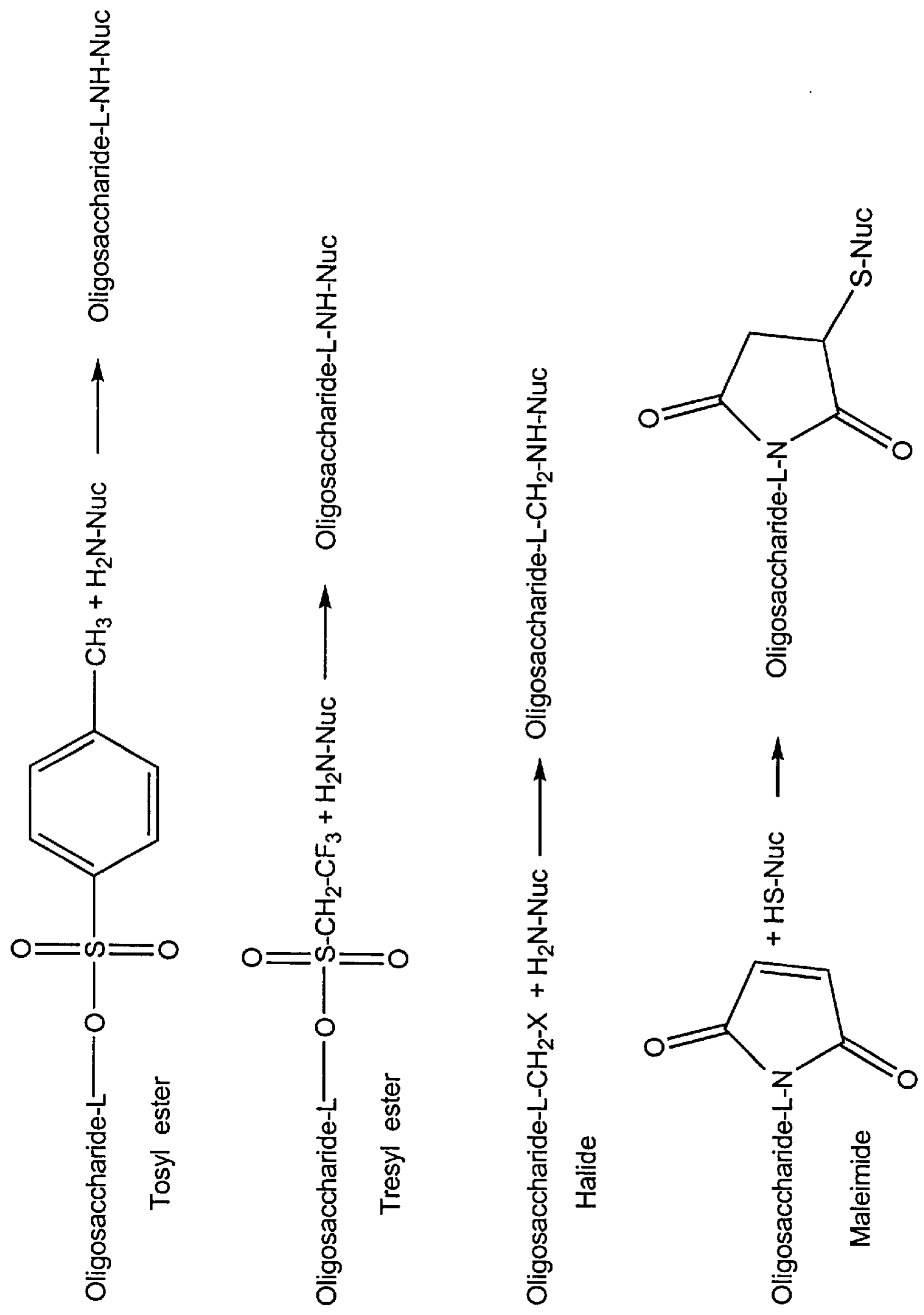
Figure 7C:
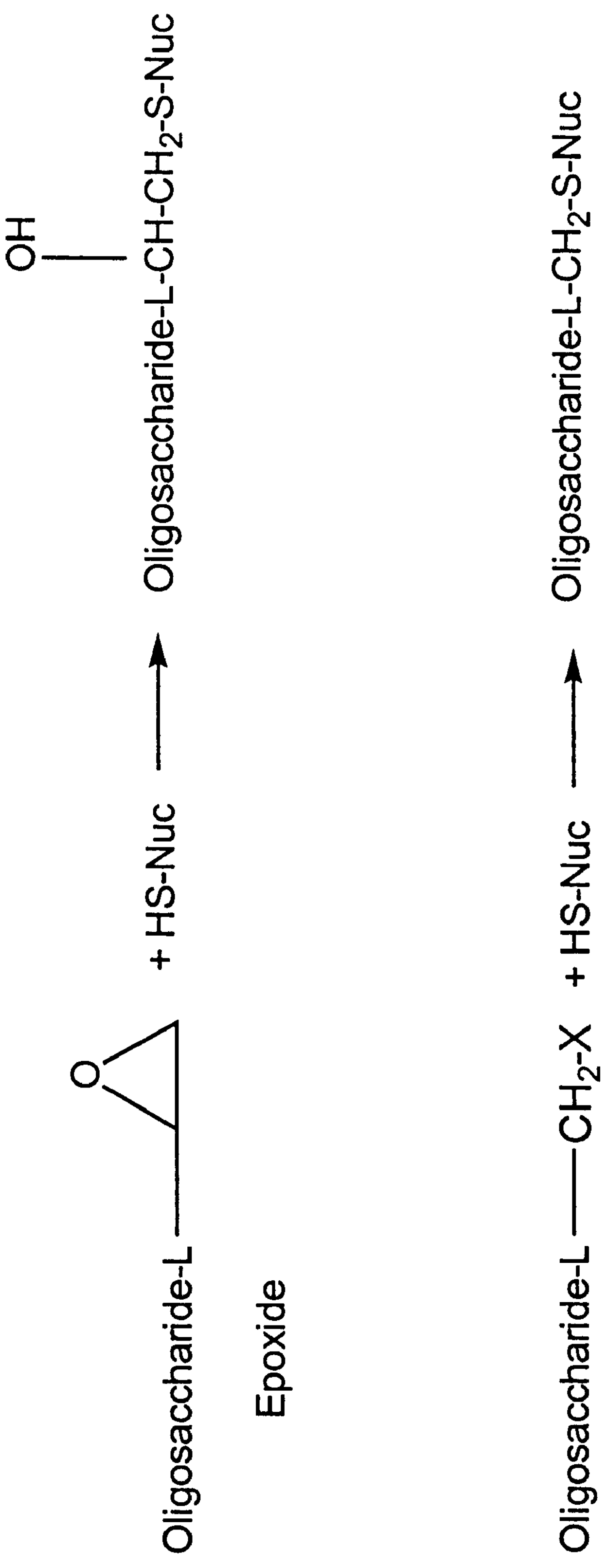

In the conjugates of the present invention, an oligosaccharide-containing reagent having a terminal electrophilic Z group as shown in FIG. 7, reacts with a nucleophilic group, such as a free amino group, on a biopolymer to produce an oligosaccharide-biopolymer conjugate. The biopolymers may be proteins including enzymes, haptens, antibodies, polypeptides; polynucleotides; steroids, and other carbohydrates. In a preferred embodiment, the biopolymer is chemically modified hemoglobin, and most preferably, diaspirin cross-linked hemoglobin. It will be apparent that use of a branched linker with two or more reactive electrophilic groups, will result in multiple anchoring of the oligosaccharide to the substrate biopolymer. The biopolymer must, of course, display one or more nucleophilic groups, either naturally occurring, or created by conventional chemical techniques. The conjugate can be purified by conventional methods. In laboratory scale, gel exclusion will separate the reactants from the conjugates in one or two steps.

Figure 1A:
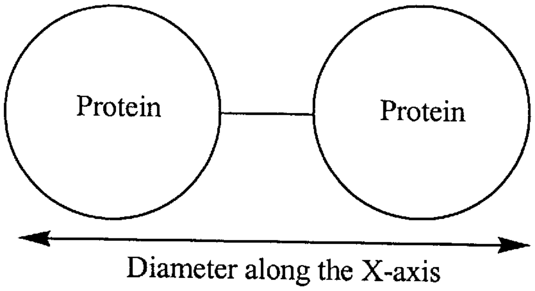
FIG. 1*a* is a schematic of two protein molecules conjugated by covalent bonding through a bridging group.
Figure 1B:
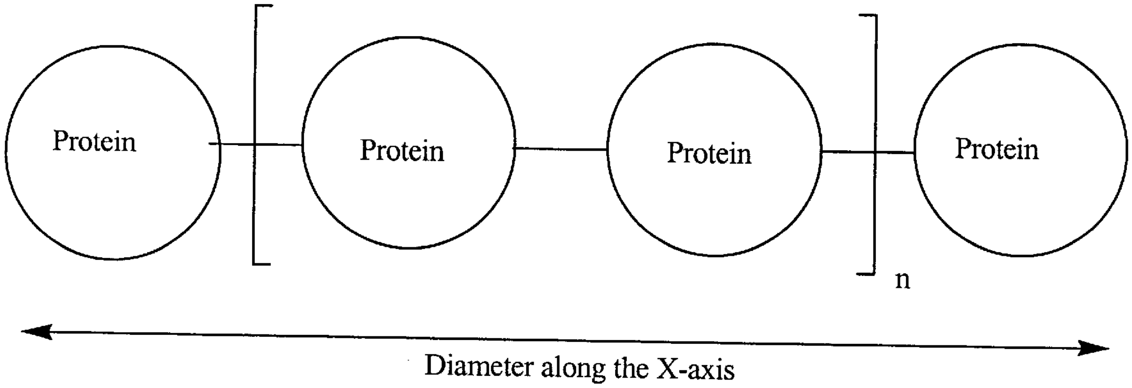
FIG. 1*b* is a schematic showing the linear characteristics of poly-conjugated protein molecules.
Figure 1C:
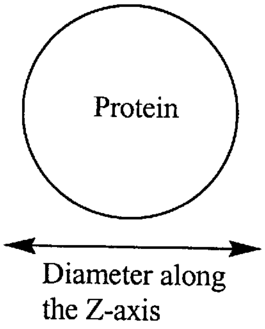
FIG. 1*c* shows the directionality of the Z axis.
Figure 2:
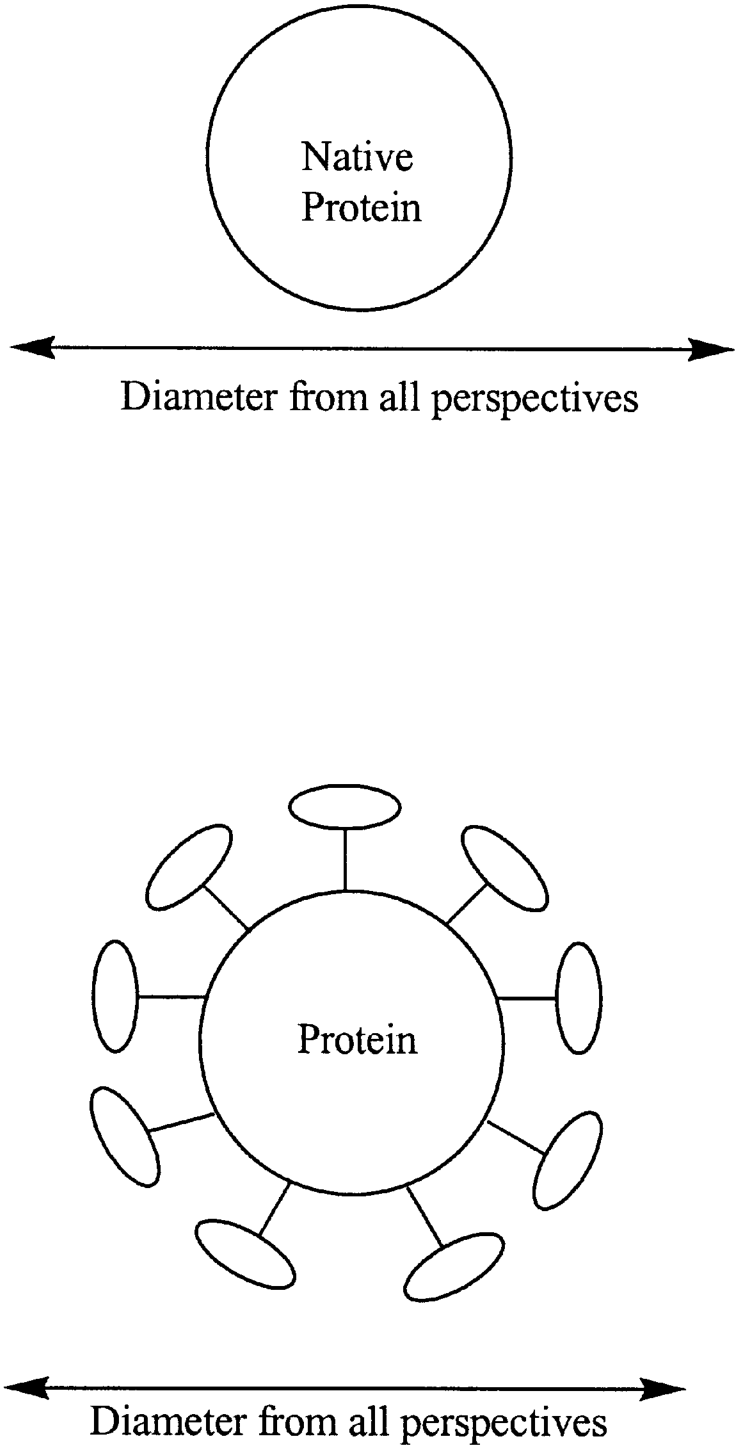
FIG. 2 shows a protein molecule decorated with surface displayed molecules.

The oligosaccharide-containing reagent having a terminal Z group is disclosed in the figures. Referring to Formula I and FIG. 1, each ring structure A, A', B and B' is a sugar. Each sugar contains at least one substituent selected from the group consisting of —$CO_2^-$, —$OSO_3^-$, —$NHCOCH_3$, and —$NHSO_3^-$. The remaining substituents on the sugar ring are selected from the group consisting of —H, glycosidic — O— and —OH. The repeating unit of the oligosaccharide comprises sugar A and sugar B, wherein sugar A is covalently joined to sugar B by a glycosidic bond from carbon-1 of sugar A to carbon-3 or carbon-4 of sugar B, wherein sugar B is covalently joined to sugar A by a glycosidic bond from carbon-1 of sugar B to carbon-3 or carbon-4 of sugar A, and n is an integer from 2 to about 20. Sugar B', which is positioned at the non-reducing terminus of the oligosaccharide has a structure identical to that of sugar B, with the exception that it is not covalently joined by a glycosidic bond at carbon-3 or carbon-4 to any other sugar. Sugar A', the erstwhile reducing sugar of the oligosaccharide, has a structure identical to that of sugar A, with the exception that the latent aldehyde that was present at carbon-1 of the sugar has been modified by reductive amination or imination to enable covalent joining to one terminus of a linker L.

The sugars A, A', B, and B' which are useful in the present invention may be commonly named as, for example, N-acetylglucosamine, glucuronic acid, N-acetylgalactosamine, iduronic acid, and glucose.

Linker L is an organic bridge having a length of from about 10 Å to about 300 Å and having a plurality of termini, one of which is covalently joined as an amine or imine to carbon-1 of sugar A' and each of the remainder of which terminates as and is covalently joined to Z, an organic functionality which provides a reaction group for covalent coupling to a nucleophile.

The organic bridge of linker L may be an acyclic, aliphatic carbon chain containing ether, thioether, or amide moieties and has a linear portion extending from sugar A' and a linear or branched portion that incorporates the remaining terminus or termini.

The purpose of the linker is to position the reactive group away from the oligosaccharide chain so as to avoid steric hinderance of the coupling reaction forming the conjugated macromolecule. It is important that the linker be aliphatic and acyclic with an absence of double bonds or aromatic rings. The incorporation of ethylene or diethylene glycol moieties, amide bonds, and thioether groups reduces antigenicity and provides for water solubility. The linker may contain one or more of these moieties as illustrated in the structures set forth in FIG. 5. The linker may be completely linear or may be branched at the terminus opposite its point of covalent attachment to sugar A'. The branched termini may each end in a Z group, to create a plurality of attachment points between the macromolecular surface and the oligosaccharide strand.

Figure 5:
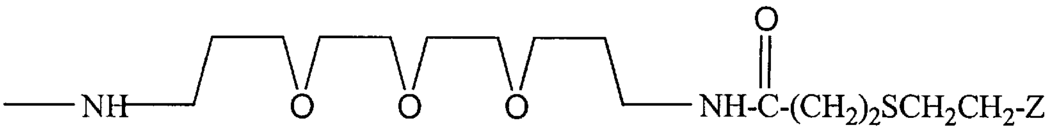
FIG. 5 shows molecular formulae for three suitable linkers.
Figure 5:
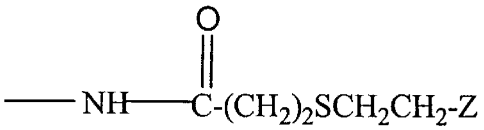
Figure 5:
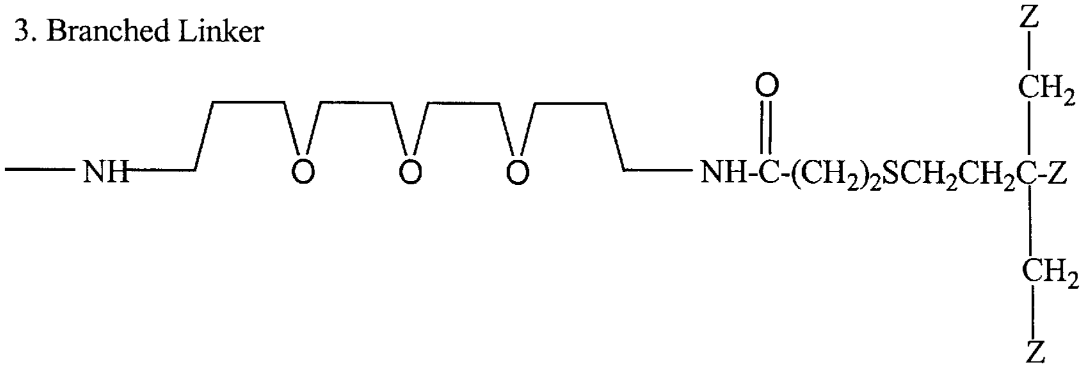

An organic functionality Z is covalently joined to each free terminus of linker L of the electrophilic reagent joined to sugar A' as shown in FIG. 5. Functionality Z will react with a nucleophile to form a covalent bond between a reagent of the present invention and the nucleophile. For example, if Z is an aldehyde, an activated ester of a carboxylic acid, a maleimide, an epoxide, a tosyl or tresyl ester, or a halide, such a reagent of the present invention will react with an amine nucleophile to yield a product in which the said reagent is covalently joined to an amine nucleophile as an imine or amine (after reduction), an amide, an amine-substituted maleimide, a beta-hydroxy amine, or an amine, respectively (see FIG. 7 for typical reactives). A Z halide, maleimide, or epoxide, will also react with a sulfhydryl nucleophile to yield a product covalently joined to the sulfhydryl nucleophile as a sulfide, a thio-substituted maleimide, or a beta-hydroxy sulfide, respectively. In the biopolymer conjugate, the Z group may be present as a residual methylene radical, β-hydroethylene radical, carboxyl radical, a succinamide alpha radical, or be absent entirely with direct joining of the linker to the biopolymer (nullity).

Many examples of these chemistries are given in *Chemistry of Protein Conjugation and Cross-linking,* S. Wong, CRC Press, Inc. (1991) which is incorporated by reference herein.

The molecular weight of the reagent of Formula 1 is from about 1,000 to about 15,000 Daltons, more preferably from about 1,000 to about 10,000 Daltons, and most preferably about 5,000 Daltons. The oligosaccharide component of Formula I may be synthesized de novo or may be derived from natural sources. In a preferred embodiment, the oligosaccharide is a hydrolysate of chondroitin sulfate. The hydrolysis is carried out conventionally, and the fragments may be sorted by known sizing methods to produce a population of desired length having less than five percent contamination by oligosaccharides of a length different from the desired length.

Substrates suitable for modification by the present reagents include peptides, proteins, nucleotides, polynucleotides, pharmaceutic agents, diagnostic agents, and polymers which have at least one nucleophilic functional group capable of forming a covalent bond with the terminus of the linker. One substrate of interest is diaspirin crosslinked hemoglobin (DCLHb) described in U.S. Pat. Nos. 4,598,064, 4,600,531, RE 34,271.

Figure 3:
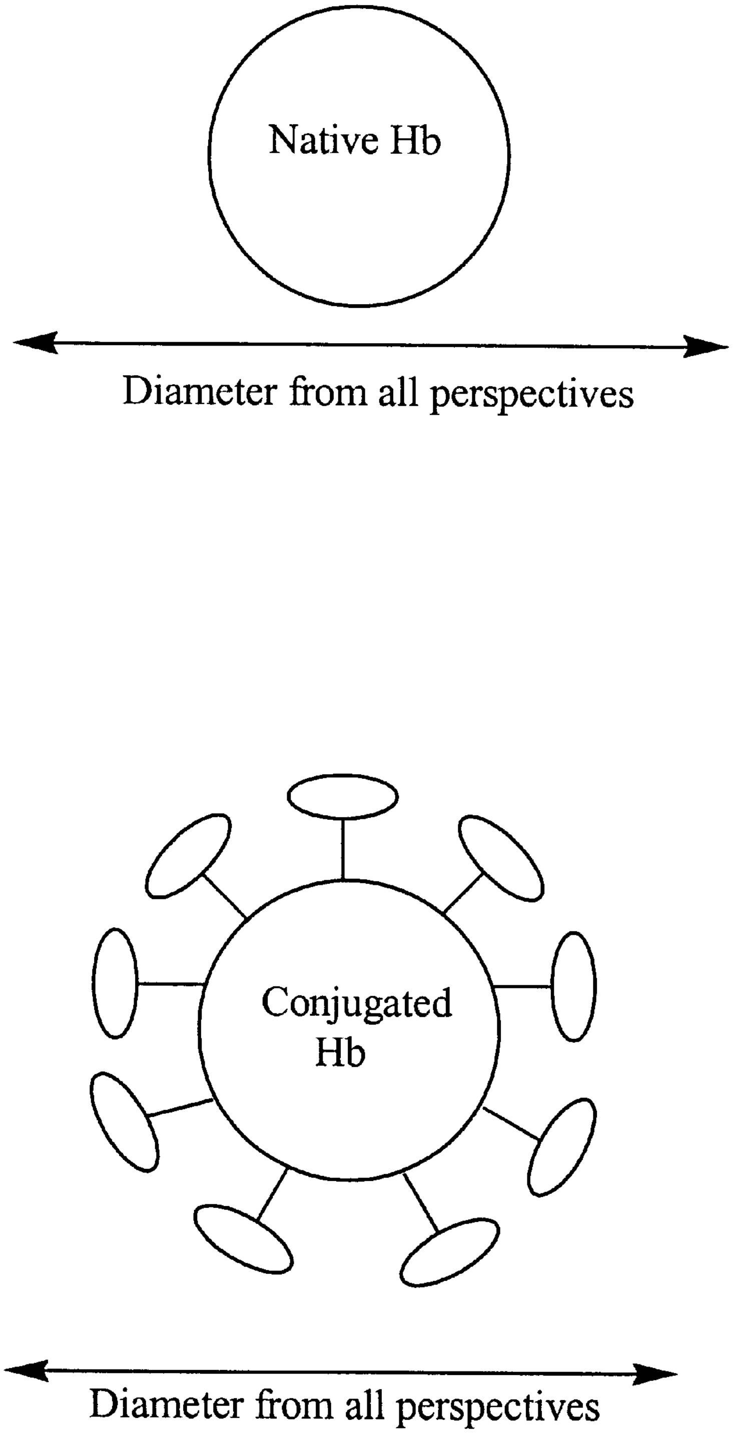
FIG. 3 limits the decorated protein to hemoglobin.
Figure 4:
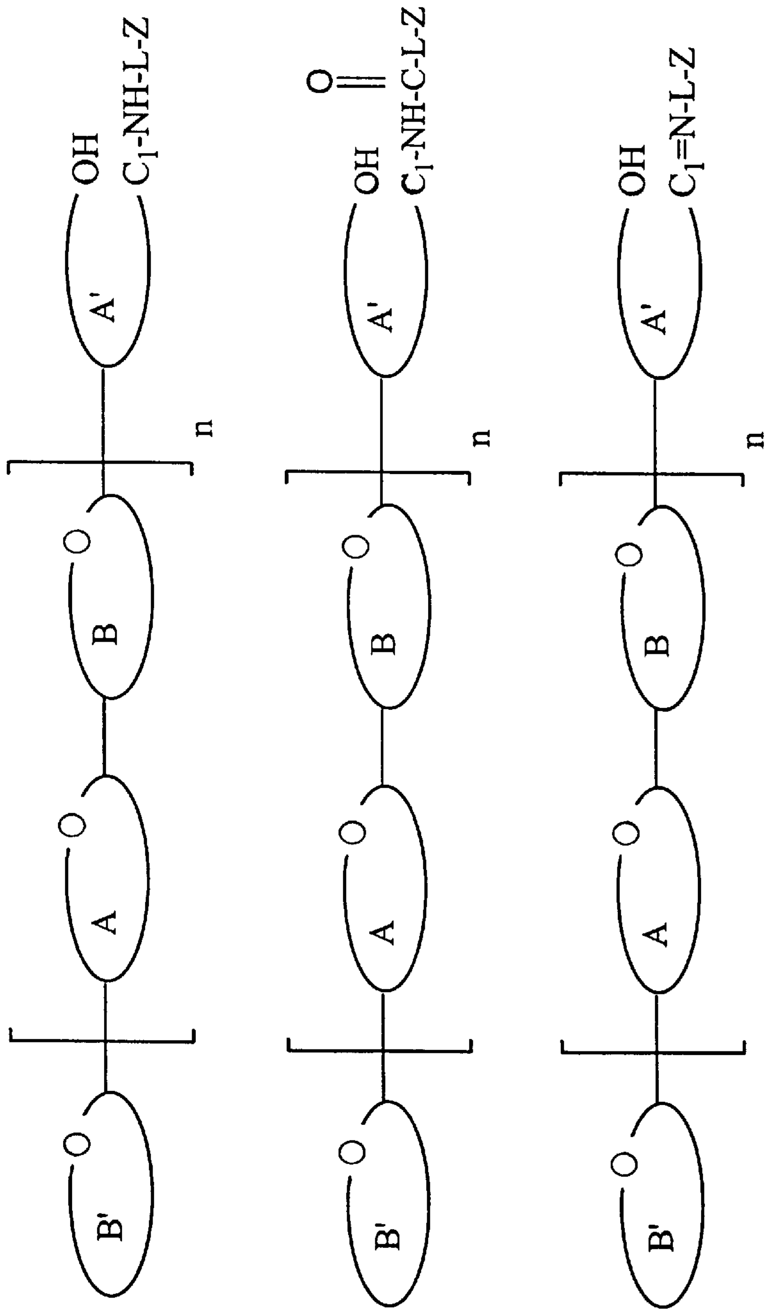
FIG. 4 gives a schematic structure for disclosed compounds showing the configuration of the modified sugar A' at the reducing termini of the amino, amido, and imino forms.
Figure 6A:
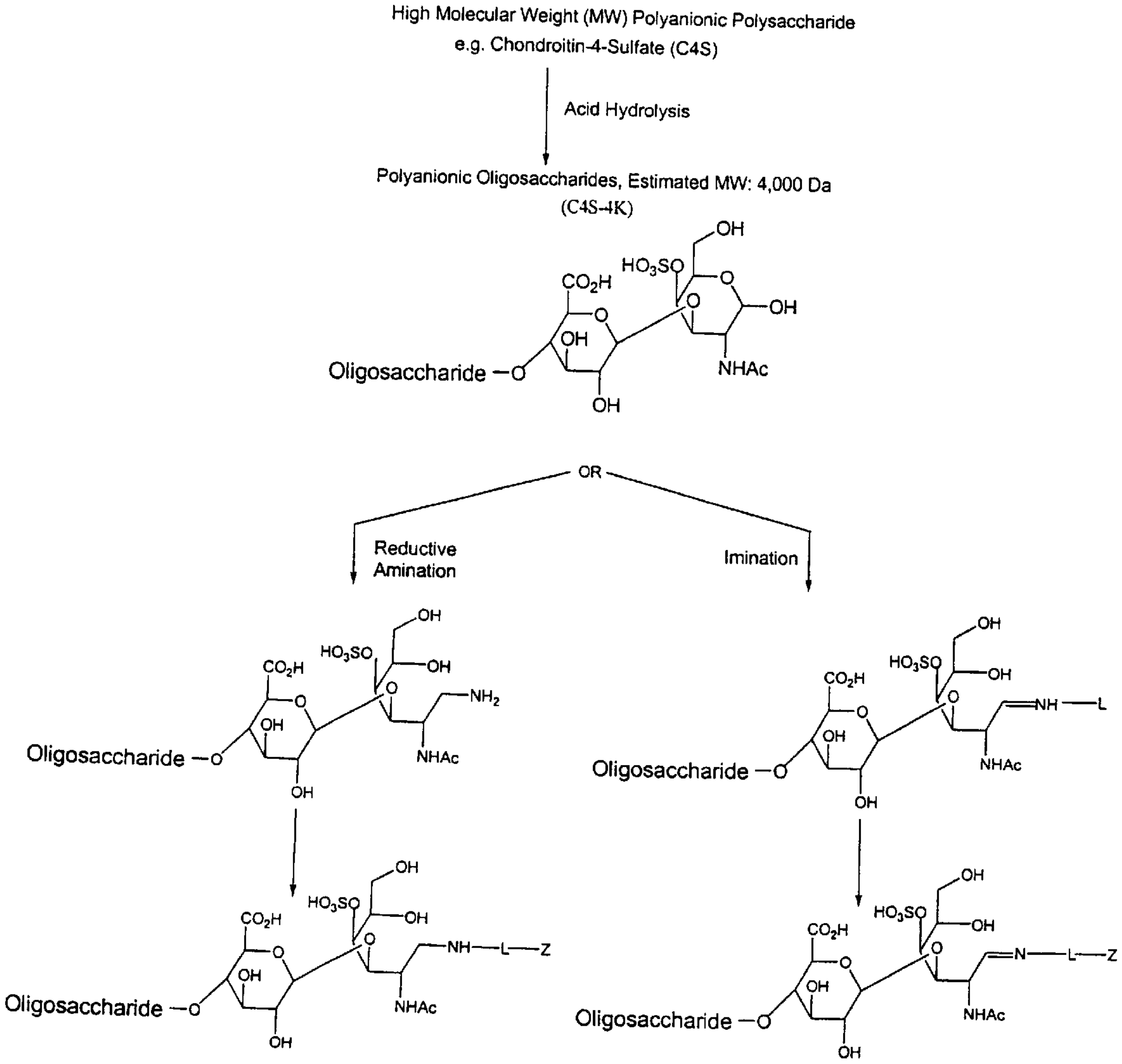
FIGS. 6*a,* 6*b* and 6*c* shows the chemistries of the reducing end moieties starting with three different native polysaccharides.
Figure 6B:
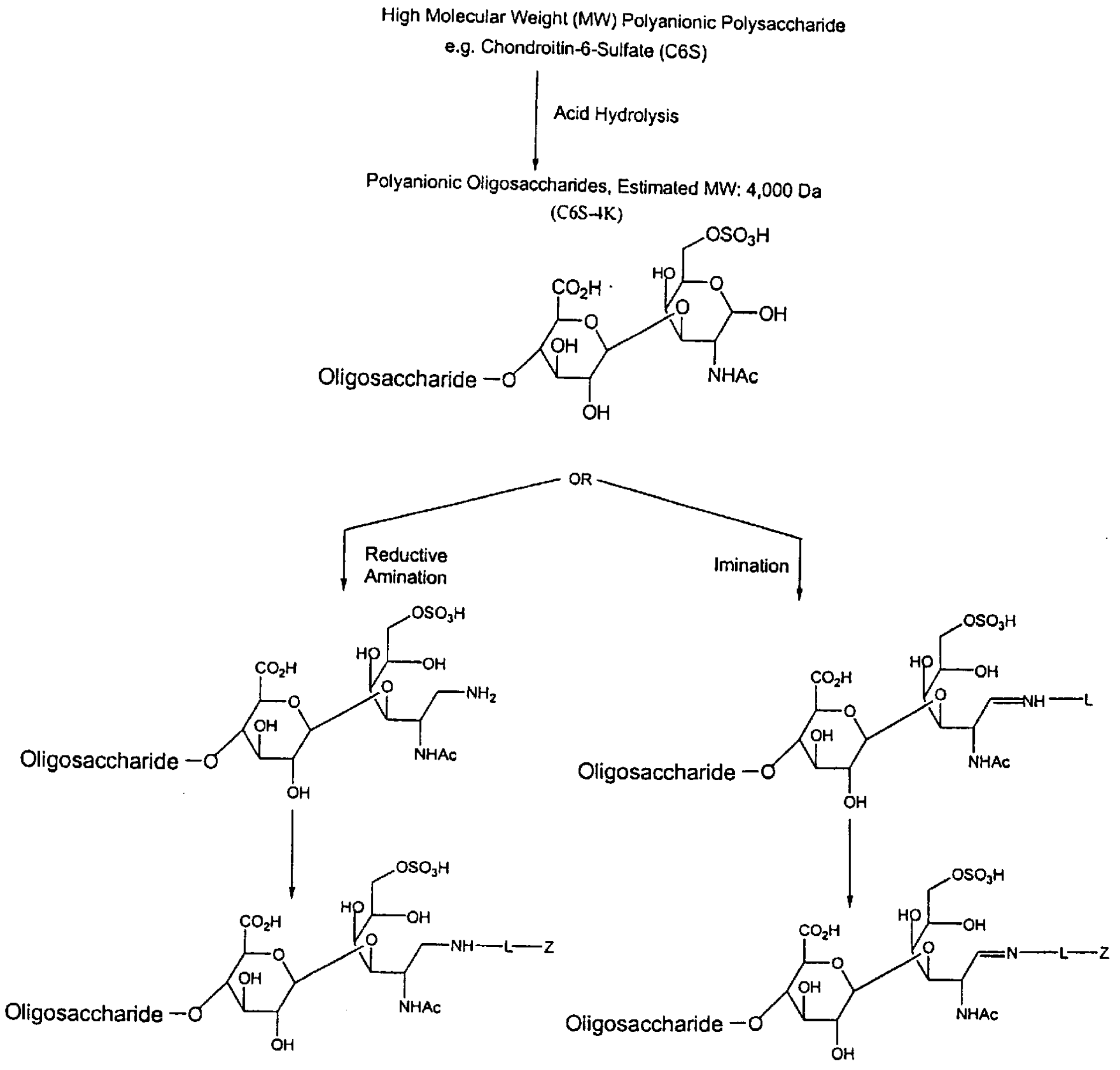
Figure 6C:
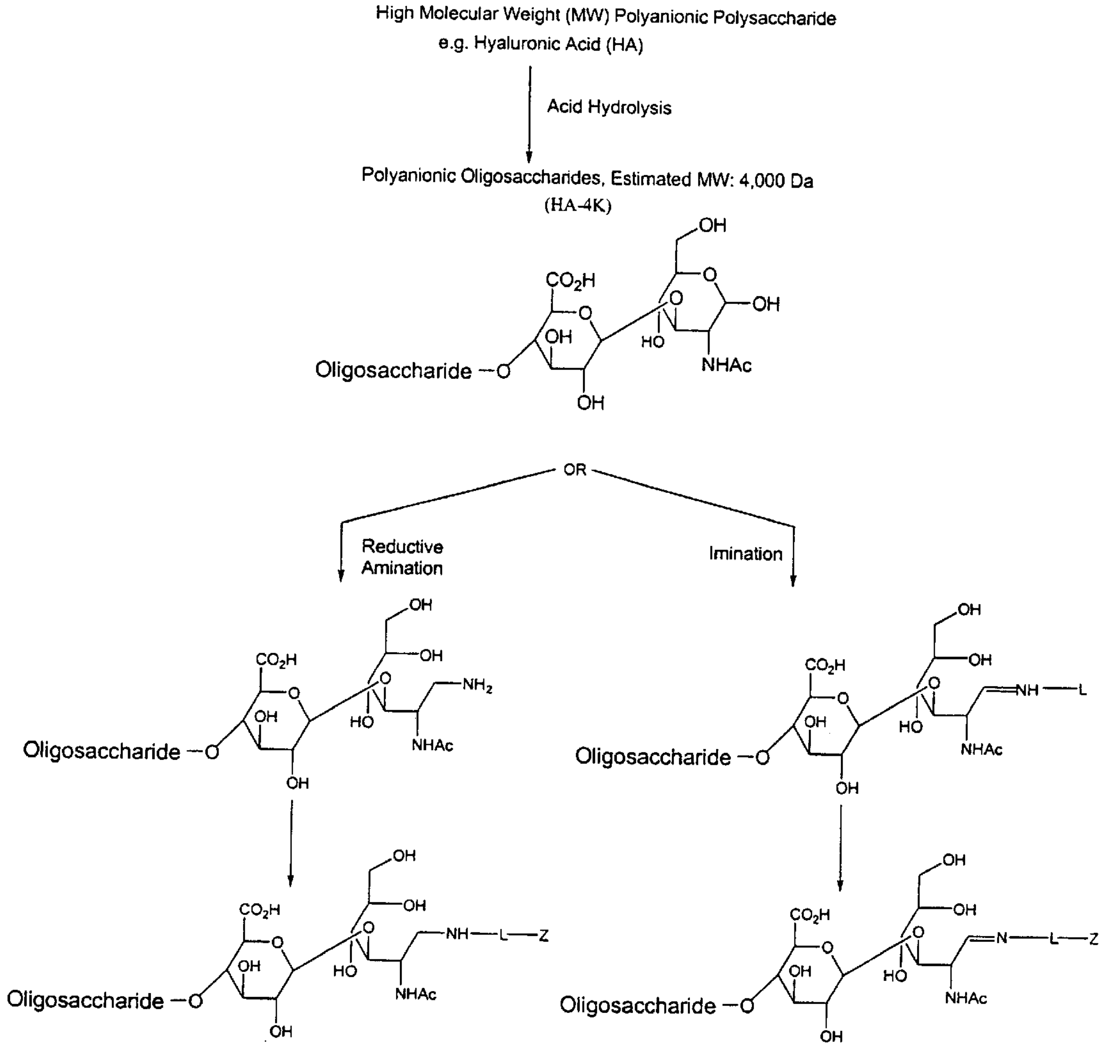

FIGS. 6*a*, 6*b* and 6*c* are flow diagrams showing structures of compounds provided in the reaction pathway in the synthesis of three reagent compounds. In FIG. 3*a* the starting material is an acid hydrolysate (polyanionic oligosaccharides) derived from chondroitin-4-sulfate. The terminal sulfate sugar is converted by reductive amination or imination to the structures shown, and then further reacted with the linker moiety containing a Z reaction group. Z reaction groups comprise an aldehyde, activated ester of a carboxylic acid, maleimide, tosyl ester, tresyl ester, halide, or epoxide. As depicted in the equation shown in FIG. 7, the Z group reacts with either an amino nucleophile or sulfhydryl nucleophile to form a bond covalently coupling the oligosaccharide linker moiety to the protein or other macromolecule.

The polyanionic oligosaccharide portion of the reagents is selected to mimic the structure and properties of glycosaminoglycans found naturally in the extracellular matrix. Thus, the polyanionic oligosaccharides are linear sugars, have a non-reducing terminus and a terminus opposite the non-reducing terminus, and are constructed from a repeating disaccharide unit. The two sugars of the disaccharide unit are joined covalently by a glycosidic bond between C-1 of one sugar and C-3 or C-4 of a second sugar and each sugar of each repeating disaccharide unit is joined covalently by a glycosidic bond to another sugar.

The oligosaccharide portion of the reagents may be obtained by acid or enzyme catalyzed hydrolysis of natural polysaccharides or may be synthesized de novo. For example, the polyanionic polysaccharides chondroitin 6-sulfate, chondroitin-4-sulfate or hyaluronic acid may be hydrolyzed with acid catalysis to a mixture of polyanionic oligosaccharides and the fragments may be sorted by known sizing methods to produce a population of desired length. In the case of chondroitin-6-sulfate the repeating disaccharide is N-acetylgalactosamine-6-sulfate joined covalently by a glycosidic bond to glucuronic acid.

In the case of chondroitin-4-sulfate the repeating disaccharide is N-acetylgalactosamine-4-sulfate joined covalently by a glycosidic bond to glucuronic acid. In the case of hyaluronic acid the repeating disaccharide is N-acetylglucosamine joined covalently by a glycosidic bond to glucuronic acid.

Likewise, starch may be hydrolyzed with acid or enzyme catalysis to a mixture of oligosaccharides and the fragments may be sorted by known sizing methods to produce a population of desired length. The selected population of fragments may be sulfated by conventional means to produce a polyanionic oligosaccharide having repeating disaccharide units comprised of glucose and sulfated glucose joined covalently by glycosidic bonds.

FIGS. 6*b* and 6*c* show the reaction and compounds formed where the starting materials are acid hydrolyzed chondroitin-6-sulfate and hyaluronic acid, respectively. In each case, a linker has a reaction Z group at its non-sugar terminus.

The conjugates of the present invention are represented schematically by Formula II:

$$B'\text{-}(A\text{-}B)_n\text{-}A'\text{-}NH\text{-}L\text{-}Y\text{-Biopolymer}$$

in which the letters common to Formula I and II have the same range of identity as disclosed for Formula I. Y herein represents either a nullity (i.e., a covalent bond links the —NH group to the biopolymer) (wherein the electrophilic group Z is a leaving group, as in halide) or that portion of Z which is incorporated into the conjugate upon reaction with the nucleophilic group on the biopolymer.

Because of the broad distribution in the body, the hemoglobin compositions of the instant invention can also be used therapeutically to deliver drugs and for in vivo imaging. Moreover, the properties of fluorescence and oxygen-binding which are inherent to hemoglobins are maintained in the hemoglobin compositions of the present invention. Therefore, the compositions are useful for photodynamic therapy, in vivo monitoring by magnetic resonance and fluorescence, and for the generation of oxygen radical species by irradiation.

Because the hemoglobin composition of the instant invention can be formulated in a balanced, physiological electrolyte vehicle which will have osmolality, onconicity, and solution pH in physiologically useful ranges and which will maintain the capability for oxygen transport and delivery in extravascular circuits, said hemoglobin compositions can be useful for the perfusion of organs and tissues isolated from the normal vasculature. In these cases, the hemoglobin composition of the present invention can supply oxygen for the maintenance of metabolic function in said organs and tissues and can remove non-oxygen ligands that may be released from said organs and tissues.

A typical dose of the hemoglobin composition of the instant invention formulated as a blood replacement fluid is from about 10 mg to 20 g or more of acellular hemoglobin per kilogram of patient body weight. Thus, a typical dose for a human patient might be from a few grams to over 300 grams of acellular hemoglobin. It will be appreciated that the unit content of active ingredients contained in an individual dose of each dosage form need not in itself constitute an effective amount, since the necessary effective amount could be reached by administration of a plurality of administrations as injections, etc. The selection of dosage depends upon the dosage form utilized, the condition being treated, and the particular purpose to be achieved according to the determination of the ordinarily skilled artisan in the field.

Administration of an acellular hemoglobin composition can occur for a period of seconds to hours depending on the purpose of the hemoglobin usage. For example, as a blood delivery vehicle, the usual time course of administration is as rapid as possible. Typical infusion rates for hemoglobin solutions as blood substitutes replacements can be from about 100 mL to 3000 mL/hour. However, when used to stimulate hematopoiesis, administration can last only seconds to five minutes and therefore administration rates can be slower because the dosage of hemoglobin is much smaller than dosages that can be required to treat hemorrhage.

The composition of the present invention can also be used for a number of in vitro applications. Non-pharmaceutical compositions of the invention can be used as, for example, reference standards for analytical instrumentation or methods, reagent solutions, means for control of gas content of cultures of cells or microorganisms, and means for removal of oxygen from solutions. For example, the delivery of oxygen by the composition of the instant invention can be used for the enhancement of cell growth in cell culture by maintaining oxygen levels in vitro. Moreover, the hemoglobin of the instant invention can be used to remove oxygen from solutions requiring the removal of oxygen, and as reference standards for analytical assays and instrumentation.

The following examples are provided by way of describing specific embodiments of the present invention.

Example 1

Preparation of Representative Oligosaccharides

In the examples, two chromatographic methods were used to monitor reactions and to characterize the products. Size-exclusion chromatography (SEC) was performed using SUPERDEX™ 200 column (Pharmacia), a mobile phase consisting of 50 mM phosphate, pH 7.0, containing 0.15 M NaCl, delivered at a flow rate of 0.7 mL/min., and analyte detection at 214 nm for oligosaccharide reagents and at 280 nm for modified peptide or protein. In this assay, materials elute from the stationary phase in the order from largest to smallest in size, i.e., larger entities elute with shorter retention times and smaller entities elute with longer retention times. Reversed-phase high performance liquid chromatography (RP-HPLC) was performed using a Vydac Protein C-4 column, with elution using mobile phases (A) and (B) delivered at 1 mL/min. as a linear gradient having the following compositions over time: 1) 50% B to 55% B over 20 minutes; 2) 55% B to 75% B over 10 minutes; 3) 75% B to 85% B over 10 minutes. Mobile phase (A) consisted of $CH_3CN/H_2O/TFA$, 20:80:0.1, by volume. Mobile phase (B) consisted of $CH_3CN/H_2O/TFA$, 60:40:0.1, by volume. Analytes were monitored at 280 nm.

A. Preparation of a Representative Oligosaccharide from Chondroitin-4-Sulfate.

Chondroitin-4-sulfate (400.8 g) was dissolved in 5 L of 0.5 N HCl. The solution was heated to 65° C. for about 24 hours and then cooled to ambient temperatures using an external ice bath. The solution pH was adjusted to 7.6 by the addition of 5 N NaOH. To the solution was added 12 L of ethanol. An oily precipitate formed. The solvent was decanted, and 4 L of ethanol was added. The mixture was stirred to obtain a granular solid. The solid was collected by filtration and washed successively with ethanol (2×500 mL) and ethyl ether (1×500 mL). The solid was dried under vacuum to give 343.5 g of product having an SEC retention time of about 27 minutes. This material was identified by the acronym "C4S-4K".

B. Preparation of a Representative Oligosaccharide from Chondroitin-6-Sulfate.

Chondroitin sulfate, Type C (18.4 g; from shark cartilage, reported molecular weight of 25–50 kiloDaltons; Maruha Corporation) was dissolved in 0.5 N HCl (230 mL), and the stirred solution was heated at 65° C. for 24 hours. The reaction mixture was cooled to room temperature, and then the solution pH was adjusted to pH 7.4 with 5 N NaOH (25 mL). The stirred solution was slowly diluted with ethanol (600 mL) and then maintained at 5° C. for three hours before the supernatant was removed by decantation. The oily residue was stirred with ethanol (200 mL) for 10 minutes and the supernatant was discarded. The residue was stirred vigorously with ethanol (400 mL) to precipitate the product, which was collected by filtration, washed successively with ethanol and ethyl ether and dried under high vacuum. The product (18.12 g) has a SEC profile characterized by a peak having a retention time (at the peak maximum) of about 27 minutes. This material was identified by the acronym "C6S-4K".

C. Preparation of a Representative Oligosaccharide from Hyaluronic Acid.

A viscous slurry of hyaluronic acid (18.4 g, Bioiberica) in 0.5 N HCl (300 mL) was stirred vigorously at 65° C. The reaction was monitored by SEC. After heating at 65° C. for 19 hours, the reaction mixture was cooled to room temperature, and the solution pH was adjusted to 7.4 with 5 N NaOH (29 mL). The solution was filtered through 0.45$\mu$ pore-size filter membrane, and the filtrate volume was reduced to 180 mL by evaporation under high vacuum. The solution was stirred during slow dilution with ethanol (750 mL) to give an oily product. After discarding the supernatant, the oily product was stirred with fresh ethanol (300 mL) to give a granular solid (14 g), which was collected by filtration, washed with ethanol and then ethyl ether, and dried under high vacuum. The product was characterized by an SEC retention time (peak maximum) of 26 minutes. This material was identified by the acronym "HA-4K".

Example 2

Reductive Amination of Representative Oligosaccharides

A. Preparation of C4S-4K-DGBE.

The reagent, diethylene glycol bis(3-aminopropyl)ether mono-t-butyl carbonate (DGBE-BOC) was prepared by known methods from diethylene glycol bis(3-aminopropyl) ether (DGBE) and di-t-butyl carbonate.

C4S-4K (222.0 g, 55.0 mmol) and DGBE-BOC (150.1 g, 470.5 mmol) were dissolved in 1.2 L of Sterile Water for Irrigation, USP, and the pH of the solution was adjusted to 8.31 by the addition of 1.00 N HCl. Ethanol (600 mL) was added to clarify the solution. Borane-pyridine complex (8 M, 57 mL) was added to the solution. The reaction was monitored by TLC (silica gel; eluent: 2-propanol:$NH_4OH$:$H_2O$, 6:1:3, by volume; detection by exposure to 2,3,5-triphenyltetrazolium chloride). The solution was heated at 40° C. for four days and then cooled to ambient temperatures. The solution pH was adjusted to 10.03 by the addition of 5.00 and 1.00 N NaOH. Ethanol (12 L) was added, and the resulting slurry was stirred for three hours. The precipitate was allowed to settle for about one hour, the solvent was decanted, and the solid was collected by filtration and washed successively with ethanol (2×500 mL) and ethyl ether (1×500 mL). The solid was dried under vacuum to constant weight (210.7 g). This material was identified by the acronym "C4S-4K-DGBE-BOC". Removal of the BOC group was achieved by treatment of C4S-4K-DGBE-BOC with fifteen equivalents of HCl in water at pH 0.8 for 24 hours to afford the desired product, which was identified by the acronym "C4S-4K-DGBE".

B. Preparation of C6S-4K-DGBE.

A solution of C6S-4K (17 g, 4.25 mmol) and BOC-DGBE (13.62 g, 42.5 mmol) in deionized water (85 mL) was adjusted to pH 8.4 with 1 N HCl (38 mL). Borane-pyridine complex (8 M, 42.5 mmol, 5.31 mL) and ethanol (30 mL) were added successively, and the clear solution was stirred at 40° C. The reaction was monitored by TLC (silica gel; eluent: 2-propanol:$NH_4OH$:$H_2O$, 6:1:3, by volume; detection by exposure to 2,3,5-triphenyltetrazolium chloride). After four days, the reaction mixture was cooled to room temperature, and the solution pH was adjusted to 10.0 with 1 N NaOH (22 mL). Water (25 mL) was added, and the solution slowly was diluted with ethanol (1 L) to precipitate the product, which was identified by the acronym "C6S-4K-DGBE-BOC". The latter (15.8 g) was collected by filtration, washed successively with ethanol and ethyl ether and dried under high vacuum. Dilute (1 N) HCl (52.2 mL) was added to a solution of C6S-4K-DGBE-BOC (13.9 g) in water (50 mL) to give a solution having a pH of 0.80. After stirring at room temperature for 24 hours, the solution was evaporated to dryness. The residue was dried under high vacuum to give solidified product (13.2 g), which was identified by the acronym "C6S-4K-DGBE".

C. Preparation of HA-4K-DGBE.

HA-4K (10.0 g, 2.5 mmol) and BOC-DGBE (7.3 g, 23.8 mmol) were combined in 50 mL of water. The pH was adjusted to 8.25 with 1.00 N HCl. Borane-pyridine complex (8 M, 3.0 mL) was added, followed by 25 mL of ethanol. The solution was heated at 40° C. for five days. The solution was cooled to ambient temperature, and the pH was adjusted to 10.00 with 1.00 N NaOH. To the solution was added 500 mL of ethanol. The solid was collected after stirring for two hours. The solid was washed with ethanol (50 mL) and then with 100 mL of ethyl ether. The solid was dried under reduced pressure to give 9.5 g of the desired product, which was identified by the acronym "HA-4K-DGBE-BOC". An 8.5 g portion of this BOC-derivative was dissolved in 35 mL of water, and 35 mL of 1.00 N HCl was added. The pH of the solution was 0.85. The solution was stirred at room temperature for about 24 hours and then concentrated under vacuum to a volume of about 100 mL. Ethanol (800 mL) was added. The mixture was stirred, and after about 1.5 hours the solid was collected and washed with ethyl ether (25 mL). The solid was dried under reduced pressure to give 6.3 g of the desired product, which was identified by the acronym "HA-4K-DGBE".

D. Preparation of C4S-4K-$NH_2$.

Borane-pyridine complex (4.7 mL, 8 M, 37.5 mmol) and ethanol (50 mL) were added to a solution of C4S-4K (15 g, 3.75 mmol) and an ammonium salt (168.75 mmol) such as ammonium acetate, ammonium bicarbonate, ammonium carbonate, ammonium carbamate or ammonium formate, for example, in water (100 mL). The solution was stirred and heated at 40–50° C. for four days. Analysis of the product mixture by TLC showed that the product mixture was negative to 2,3,5-triphenyltetrazolium chloride (a reagent for the detection of reducing sugars) and positive to ninhydrin. Then the reaction mixture was concentrated under vacuum to dryness and the residue was successively treated with water (100 mL) and concentrated under vacuum to dryness (3 times) to remove excess ammonium salt. The residue was dissolved in water (150 mL) and the solution was diluted with ethanol (600 mL) to give an oily product which was isolated by decantation. The oily product was stirred with ethanol (400 mL) to solidify the product, which was isolated by filtration, washed with ethyl ether, and dried under vacuum to constant weight (13.5 g). This material was identified by the acronym "C4S-4K-$NH_2$".

E. Preparation of C6S-4K-$NH_2$.

It is chemically reasonable to predict that treatment of C6S-4K with an ammonium salt in the presence of a reducing agent such as borane-pyridine in the manner described above will yield the amine "C6S-4K-$NH_2$".

F. Preparation of HA-4K-$NH_2$.

Borane-pyridine complex (BP; 2.12 mL; 8 M; molar ratio of BP/HA-4K of 10) and ethanol (25 mL) were added to a solution of HA-4K (6.8 g; 1.7 mmol; assumed MW of 4000) and ammonium carbonate (7.35 g, 76.5 mmol) in water (60 mL). The solution was stirred at 40° C. for five days and evaporated to dryness. The residue was dissolved in water (50 mL), and the solution was extracted with chloroform (3×50 mL) to remove excess boranepyridine. The aqueous solution was concentrated under vacuum to dryness, and the residue was treated with water (4×50 mL) and reconcentrated to dryness to remove residual ammonium carbonate. The resulting residue was dissolved in water (50 mL), the solution was filtered through 0.45 μ pore-size filter membrane, and the filtrate was diluted with ethanol (250 mL) to give an oily product. The supernatant was removed by decantation. The oily product was stirred with ethanol to give a solid (5.8 g), which was collected by filtration, washed successively with ethanol and ethyl ether and dried under high vacuum. This material was identified by the acronym "HA-4K-$NH_2$".

Example 3

Preparation of Representative Reagents of the Instant Invention

A. Synthesis of the Aldehyde Derivative C4S-4K-DGBE-TPA.

N-Succinimidyl-4-thia-7-diethoxyheptanoate was prepared from 4-thia-7-diethoxyheptanoic acid using known methods. 4-Thia-7-diethoxyheptanoic acid was prepared by the condensation of methyl 3-mercaptopropionate (120.0 g, 1.0 mol) with 3-chloropropionaldehyde diethyl acetal in the presence of potassium carbonate (250.0 g, 1.8 mol) in 1 L of DMF and base-catalyzed hydrolysis of the ester using known methods.

C4S-4K-DGBE (140.0 g, 35.0 mmol) was dissolved in 1.2 L of water. The pH of the solution was adjusted to 9.10 with 5.00 NaOH. N-Succinimidyl 4-thia-7- diethoxyheptanoate (58.8 g, 170.0 mmol) in 500 mL of DMF was added dropwise. After the addition was complete, the solution was stirred four hours at ambient temperatures. The volume of solvent was reduced to about 500 mL by rotary evaporation. Ethanol (4 L) was added to the residual concentrate. The solution was decanted. Ethanol (4 L) was added and the mixture was kept at 5° C. The solvent was decanted. The resulting mixture was centrifuged to give a gel-like pellet. The pellet was diluted with acetone and evaporated to a semi-solid. Ethyl ether was added and the mixture was allowed to stand for one hour. The mixture was filtered and the gel-like solid was dried under vacuum at ambient temperatures. The solid was collected to give 104.7 g of product, an acetal which was identified by the acronym "C4S-4K-DGBE-TPDA".

C4S-4K-DGBE-TPDA (104.3 g) was dissolved in 750 mL of sterile water and 750 mL of 1.00 N HCl. The pH of the solution was adjusted to 2.00 with 1.00 N HCl. The solution was stirred for 3.5 hours. The reaction solution was concentrated under vacuum to a volume of about 100 mL. Acetone (250 mL) was added to precipitate the product as an oil. The solvent was decanted and an additional 250 mL of acetone was added. The mixture was agitated and the solvent was decanted. To the resulting semi-solid was added an additional 250 mL of acetone. The mixture was allowed to stand for one hour. The resulting solid was collected and washed with 100 mL of acetone. The solid was dried under vacuum to give 113.6 g of product, which was identified by the acronym "C4S-4K-DGBE-TPA". The product exists in the aldehyde and hydrated form and contains residual solvent.

B. Synthesis of the Aldehyde Derivative C4S-4K-DGBE-SBA.

C4S-4K-DGBE (10.0 g, 2.5 mmol) was dissolved in 100 mL of water, and the solution pH was adjusted to 9.31 with 1.00 N NaOH. N-Oxysuccinimidyl N-(4-diethoxy) butyrylsuccinamate (4.5 g, 12.5 mmol) in 10 mL DMF was added to the reaction solution. The solution was stirred for 3 hours at room temperature. The solution was reduced in volume under vacuum to about 25 mL. To the solution was added 1 L of ethanol. The slurry was cooled to 5° C. overnight. The solvent was decanted, and the solid was collected by filtration. The solid was washed with ethanol (25 mL) and then ethyl ether (2×25 mL). The solid was dried under vacuum to give 6.8 g of product, which was identified by the acronym "C4S-4K-DGBE-SBDA". A 5.5 g (1.4 mmol) portion of this material was dissolved in 25 mL of water, and the solution pH was adjusted to 1.50 with 1.00 N HCl. The solution was stirred at room temperature for four hours. The volume of solution was reduced to about 10 mL by evaporation under vacuum. Acetone (50 mL) was added. The solvent was decanted, and an additional 50 mL of acetone was added. The solvent was decanted and 50 mL of acetone was added. The mixture was stirred, and the solid was collected by filtration. The solid was dried to give 5.0 g of the desired product. This material was identified by the acronym "C4S-4K-DGBE-SBA".

C. Synthesis of the Maleimide Derivative C4S-4K-DGBE-MP.

A solution of C4S-4K-DGBE (7 g, 1.75 mmol) in water (46 mL) and N,N-dimethylformamide (DMF; 23 mL) was added to a stirred solution of N-succinimidyl maleimidopropionate (SMP; 2.78 g, 10.5 mmol) in DMF(140 mL) and water (10 mL) at a rate of 4.5 mL/minute. After the addition was complete, the solution was stirred for an additional one hour. The reaction mixture was evaporated to dryness. The residue was dissolved in water and filtered to removed an insoluble material. The filtrate was diluted with ethanol to precipitate the product (5.83 g), which was identified by the acronym "C4S-4K-DGBE-MP".

D. Synthesis of the Aldehyde Derivative C6S-4K-DGBE-TPA.

The pH of a solution of C6S-4K-DGBE (12 g, 3.0 mmol) in water (75 mL) was adjusted to pH 10.0 with 1 N NaOH (43 mL). To this stirred solution was added, dropwise a solution of N-succinimidyl 4-thia-7-diethoxy-heptanoate (6.06 g, 18 mmol) in DMF (150 mL). After the addition was completed, the reaction mixture was stirred for three hours at room temperature. Then the solvent was removed by rotary evaporation. Water (100 mL) was added, and the solution was diluted with ethanol (400 mL) to precipitate the product (10 g), an acetal derivative which was identified by the acronym "C6S-4K-DGBE-TPDA". This product was collected by filtration, washed successively with ethanol and ethyl ether and dried under vacuum. Then a 10 g portion was dissolved in 0.1 N HCl (189 mL) to give a solution having a pH of 2.0. The solution was stirred at room temperature for three hours and then evaporated to dryness. The residue was dried under high vacuum at 35° C. to give solidified product (identified by the acronym "C6S-4K-DGBE-TPA; 9.8 g) which existed as a hydrated aldehyde.

E. Synthesis of the Aldehyde Derivative HA-4K-DGBE-TPA.

HA-4K-DGBE (6.0 g, 1.5 mmol) was dissolved in 50 mL of water, and the solution pH was adjusted to 9.15 with 5 N NaOH. N-Oxysuccinimidyl 4-thia-7-diethoxyheptanoate (2.7 g, 9 mmol) in N,N-dimethylformamide (20 mL) was added. The solution was stirred for three hours. The solution was evaporated to about 10 mL. Water (20 mL) was added and the solution was evaporated to 10 mL. Ethanol (500 mL) was added and the solution was stirred. The mixture was kept at 5° C. overnight. The solvent was decanted and the solid was collected by filtration. The solid was washed with ethanol (2×25 mL) and then with ethyl ether. The solid was dried under reduced pressure to give 6.6 g of the desired protected aldehyde, which was identified by the acronym "HA-4K-DGBE-TPDA". A 5.0 g portion of said protected aldehyde was dissolved in 35 mL of water. The pH was adjusted to 1.50 with 1.00 N HCl. After about 2.5 hours, the solution was evaporated to about 10 mL. Ethanol (400 mL) was added. The solid was collected and washed with acetone. ($^1$H-NMR indicated that the acetal was not reformed due to the use of ethanol.) The solid was dried under reduced pressure to give 3.6 g of the desired product, which was identified by the acronym "HA-4K-DGBE-TPA".

F. Synthesis of the Aldehyde Derivative C4S-4K-TPA.

C4S-4K-$NH_2$ (13.12 g, 3.28 mmol) was dissolved in water (140 mL) to give a solution having a pH of 8.16. The solution pH was adjusted to 9.0 with 1 N NaOH (4.5 mL). To this solution was added a solution of N-succinimidyl-4-thia-7-diethoxyheptanoate (6.62 g, 19.68 mmol) in DMF (140 mL). The reaction mixture was stirred at room temperature for four hours and then evaporated to dryness. The residue was dissolved in water (100 mL) and the solution diluted with ethanol (500 mL) to give an oily product, which was isolated by decantation. Vigorous stirring of the oily product with ethanol gave a solid product (9.3 g), which was isolated by filtration, washed with ethyl ether and dried under high vacuum. This intermediate was identified by the acronym "C4S-4K-TPDA".

C4S-4K-TPDA (8.87 g) was dissolved in water (35 mL) to give a solution having a pH of 4.37. The solution pH was adjusted to 2.0 with 1 N HCl, and the solution was stirred at room temperature. Monitoring the reaction by $^1$H-NMR indicated that the reaction was completed after four hours. The reaction mixture was concentrated under reduced pressure at 35° C. to ¼ of its original volume and diluted with acetone (100 mL) to give an oily product. The latter was isolated by decantation and triturated with acetone to afford a solid product (7.75 g), which was isolated by filtration and dried under high vacuum. NMR data indicated that the product, which was identified by the acronym "C4S-4K-TPA", existed as hydrated aldehyde form.

G. Synthesis of the Aldehyde Reagent C4S-4K-ABA.

Chondroitin-4-sulfate (22.2 g, 5.55 mmol) and 4-aminobutyraldehyde diethoxyacetal (7.6 g, 47.0 mmol) were combined in 120 mL of water. The pH was adjusted to 8.35 with 1.00 N HCl. Ethanol (60 mL) was added followed by borane-pyridine complex (5.7 mL). The solution was heated at 40° C. for six days. The solution was cooled and the pH was adjusted to 10.00 with 5.00 N NaOH. To the stirred solution was added 1 L of ethanol. The mixture was stirred for two hours, and the precipitate was collected by filtration. The solid was washed with ethanol (75 mL) followed by ethyl ether (75 mL). The solid was dried under vacuum to give 21.5 g of product, which was identified by the acronym "C4S-4K-ABDA". The product was negative to 2,3,5-triphenyltetrazolium chloride, indicating that coupling between C4S-4K and 4-aminobutyraldehyde diethoxyacetal was successful. C4S-4K-ABDA (6.1 g, 1.5 mmol) was dissolved in 40 mL of water, and the solution pH was adjusted to 1.50 with 1.00 N HCl. After 2.5 hours, the volume of solution was reduced to about 15 mL by evaporation under vacuum. Acetone (150 mL) was added to the solution, and the resulting mixture was stirred for 30 minutes. The solvent was decanted, and an additional 150 mL of acetone was added. The mixture was stirred to give a solid. The solid was collected and dried under reduced pressure to 6.0 g of the desired product, which was identified by the acronym "C4S-4K-ABA".

H. Synthesis of the Aldehyde Reagent HA-4K-TPA.

HA-4K-$NH_2$ (9.0 g, 2.25 mmol) was dissolved in 90 mL, of water and the pH was adjusted to 9.15 with 1 N NaOH. N-Oxysuccinimidyl 4-thia-7-diethoxyheptanoate (3.6 g, 11.9 mmol) in DMF (20 mL) was added in one portion. An additional 20 mL of water was added. The solution was stirred for 4.5 hours, and then the volume was reduced to about 25 mL by evaporation under vacuum. Ethanol was added, and the resulting slurry was stirred for two hours. The solid was collected by filtration and was washed with ethanol (25 mL) and then with ethyl ether (25 mL). The solid was dried under reduced pressure to give 9.5 g of product, HA-4K-TPDA. A 9.5 g portion was dissolved in 65 mL of water. The pH was adjusted to 1.50 with 1.00 N HCl. After about 2 hours, the solution was filtered through a 0.2 $\mu$m pore-size nylon filter membrane, and the volume of filtrate was reduced by evaporation under vacuum to about 15 mL. Acetone (250 mL) was added, and after 30 minutes the solvent was decanted. An additional 250 mL of acetone was added. The solid was collected and washed acetone (50 mL). The solid was dried under reduced pressure to give 8.9 g of HA-4K-TPA.

I. Synthesis of the Aldehyde Reagent C4S-4K-AOA-DGBE-MP.

Both [(t-butyl-oxycarbonyl)amino]oxy]acetic acid and its activated ester derivative N-succinimidyl [[(t-butyloxycarbonyl)amino]oxy]acetate were prepared by known methods. N-Benzyl-oxycarbonyl-N'-[[[(t-Butyloxycarbonyl)amino]oxy]acetyl]-diethylene glycol bis (3-aminopropyl) ether (t-BOC-$NHOCH_2CO$-DGBE-Z) was prepared by the condensation of benzyloxycarbonyl DGBE (17.8 g, 50.4 mmol) with N-succinimidyl [[(t-butyloxycarbonyl)amino]oxy]acetate (13.2 g, 45.8 mmol) in 300 mL of chloroform in the presence of triethylamine (7.0 mL, 50.4 mmol). N-Benzyloxycarbonyl-N'-(aminoxyacetyl)-diethylene glycol bis(3-aminopropyl) ether ($H_2NOCH_2CO$-DGBE-Z) was prepared by treatment of t-BOC-$NHOCH_2CO$-DGBE-Z with trifluoroacetic acid in methylene chloride. Both N-succinimidyl 3-maleimidopropionate (SMP) and 3-maleimidopropionic acid were prepared by known methods.

C4S-4K (12.1 g) was dissolved in 40 mL of water, and a solution of $H_2NOCH_2CO$-DGBE-Z (17.5 g) in 20 mL of ethanol was added. The solution pH was adjusted to 4.5 (pH strips 0.0–6.0) using 1.00 N NaOH. The solution was heated at 40° C. for two days. The solution was allowed to return to ambient temperature, and the solution pH was adjusted to 10.5 by the addition of sodium hydroxide solution. Ethanol (800 mL) was added to the solution to precipitate the product. The solid was isolated by filtration and washed with ethanol. The solid was air dried to give 16.1 g of product, which was identified by the acronym "C4S-4K-AOA-DGBE-Z".

C4S-4K-AOA-DGBE-Z (5.075 g) was dissolved in 100 mL of water. Pd/C (0.408 g) was added, and the resulting slurry was exposed to hydrogen overnight. The reaction mixture was filtered through a pad of Celite 521, and the filtrate was evaporated to a semi-solid. The semi-solid was dissolved in about 25 mL of water. Ethanol was added to precipitate the product. The product was collected and washed with ethanol and dried under vacuum to give 4.1 g of product, which was identified by the acronym "C4S-4K-AOA-DGBE".

C4S-4K-AOA-DGBE (4.0 g, 1.0 mmol) in 60 mL of water was added dropwise to a solution of N-succinimidyl maleimidopropionate (SMP) in 100 mL of DMF. Water (15 mL) was added to achieve a homogeneous solution. The solution was stirred for one hour and the solvent was evaporated under vacuum. The residue was combined with 40 mL of water and filtered. The filtrate was combined with 600 mL of ethanol. The mixture was left to stand at ambient temperature overnight. The solid was collected and washed with ethanol (2×10 mL). The solid was dried to give 3.5 g of product, which was identified by the acronym "C4S-4K-AOA-DGBE-MP".

Example 4

In vitro Exposure of Oligosaccharide-Modified Diaspirin Crosslinked DCLHb to Red Cell Preparations.

Approximately 20 mL of human blood was freshly collected from each of several donors into an evacuated container containing ethylenediaminetetraacetate (EDTA). The blood samples from several donors were pooled in a 50 mL centrifuge tube. One milliliter portions were dispensed into several test tubes. Then a volume of electrolyte diluent (negative control) and a volume of a second test or control solution was added such that the final concentration of the test or control article was that shown in the following table. Another modified hemoglobin which is known to cause red cell aggregation in this test was employed as a positive control. The test tubes were incubated for one hour. A specimen was removed from each test tube, and a slide was prepared from that specimen and stained. Each slide was observed for red cell aggregation and scored on a scale from zero to three, where zero indicated that no aggregation was observed and three indicated that extensive, irreversible aggregation was observed, i.e., disaggregation was not observed following the addition of normal saline solution to the sample.

TABLE 1

Results of in vitro Red Cell Aggregation Testing

| Negative Control Article and Relative Concentration by Volume | Test Article and Relative Concentration by Volume | Extent of Red Cell Aggregation |
|---|---|---|
| 50% Electrolyte Diluent | | No aggregation observed (0) |
| | 10% Positive Control | Few aggregates observed (1) |
| | 30% Positive Control | Many red cell aggregates (1+) |
| | 50% Positive Control | Extensive red cell aggregation and some small platelet clumps observed (2+) |
| | 10% C4S-4K-DCLHb | None seen (0) |
| | 30% C4S-4K-DCLHb | None seen (0) |
| | 50% C4S-4K-DCLHb | None seen (0) |

This test was repeated using each of four C4S-4K-DGBE-TPA-DCLHb test articles having differing extents of hemoglobin modification. In each test, no red cell aggregation was observed in test solutions containing the oligosaccharide reagent-modified hemoglobin. The negative and positive control solutions gave characteristic responses.

Example 5

Hyperyolemic-hemodilution During Cerebral Ischemia in a Spontaneous Hypertensive Rat Model of Middle Cerebral Artery Occlusion Hemodilution has been proposed as both a prophylactic and resuscitative therapy for focal cerebral ischemia. One basis for its therapeutic benefit may be a decrease in blood viscosity and augmentation of cerebral blood flow (CBF) to the area of ischemia. When nonoxygenating fluids are employed for hemodilution, changes in hematocrit are limited to modest decreases. In contrast, when an oxygen-carrying hemoglobin solution is used, greater hemodilution may be achieved, since the oxygen delivery capacity and capabilities are maintained.

A rat model of middle cerebral artery occlusion (MCAo) and reperfusion has been used to assess the effectiveness of hemodilution with hemoglobin compositions of the present invention. In this model, spontaneously hypertensive rats were anesthetized, intubated, and mechanically ventilated. Femoral arterial and venous lines wee placed to enable monitoring of physiological parameters. An incision was made in the left cheek of the animal, and an area of temporal bone was cleared of sufficient size to visualize the MCA. A 10-0 monofilament nylon suture was used to loop around the MCA in two places, one proximal to the olfactory tract (including the rostral branch) and the second at the level of the cerebral vein. Then each rat was randomized to one of the following groups for which the blood volume was increased by 8.0 mL (~30%) and hematocrit (Hct) maintained at the desired value throughout the MCAo. In the control group, the hematocrit was not manipulated; each animal received 4 mL of 10% albumin solution and 4 mL of whole blood. In the test groups, animals were given a 3 mL exchange of infusion of the test article at a rate of 0.5 mL/min, followed by a 7.5 mL topload at a rate of 0.5 mL/min. Immediately after delivering the final volume, both loops around the MCA were secured until the MCA blanched, mimicking MCAo. The vessels in the area of the MCA were visualized, and any aggregation, clumping and/or other red cell distinction were noted. After three hours of occlusion, both sutures were cut and removed, and MCA was stroked to re-establish perfusion. The extent of reperfusion and visible red cell aggregation were noted. After two hours of reperfusion, the animal was deeply anesthetized, a thoracotomy was performed, during which 20 mL of 2& 2,3,5-triphenyltetrazolium chloride (TTC) was administered, and the descending aorta was clamped. At the completion of TTC infusion, the animal is left undisturbed for ten minutes, and then a lethal dose of a mixture of 12.5% glutaraldehyde/10% buffered formalin was administered. The animal was decapitated, and the brain was removed. The cerebrum was isolated and fixed, and tissue slices were prepared and photographed on both sides. A DUMAS Image Analysis program (Drexel University) was used to quantitate and average the extent of tissue staining by the TTC. The raw data were analyzed statistically, and final percentages were adjusted for swelling and averaged for the entire brain.

Three test articles were used in this study. DCLHb (Diaspirin Crosslinked Hemoglobin) was the negative control hemoglobin composition. PASS-DCLHb, a polymerized hemoglobin, was the positive control hemoglobin composition; PASS-DCLHb is known to cause red cell aggregation and typically demonstrates no reduction in infarct volume following MCAo. The term "CS-DCLHb" was used to identify a hemoglobin composition of the present invention (Example 4.C.) Experimental data are summarized in the Table below.

The results of this experiment may be summarized as follows. Compared to the Control group, hemodilution with DCLHb, the negative control hemoglobin composition, resulted in no red cell aggregation or other distinction and effected an approximately 50% reduction in infarct size. In contrast, hemodilution with PASS-DCLHb, the positive control hemoglobin composition, resulted in severe red cell aggregation and effected no reduction in infarct size, relative to that observed in the Control group. As was observed after hemodilution with DCLHb, hypervolemic hemodilution with the hemoglobin composition of the present invention, CS-DCLHb, caused no red cell aggregation or other distinction and effected an approximately 50% reduction in infarct size.

In addition, it was noted that CS-DCLHb seemed to have less of a detrimental effect on the percent oxygen in the blood as compared to DCLHb. Thus, animals in the DCLHb group required higher flows of oxygen than did those in the CS-DCLHb group. Moreover, the hemodilutive effect of CS-DCLHb was slightly greater and lasted longer than that of DCLHb.

TABLE 2

Effectiveness of Hemoglobin Compositions in Reduction of Infarct Size Following Middle Cerebral Artery Occlusion in a Spontaneously Hypertensive Rat Model.

| | Experimental Group | | | |
|---|---|---|---|---|
| Experimental Parameter | Control | DCLHb | CS-DCLHb | PASS-DCLHb |
| Approximate volume of hemisphere ipsilateral to MCAo | | | | |
| Infarct volume, $mm^3$ | 140 | 70 | 70 | 140 |
| Extent of red cell aggregation or blood flow abnormality: | | | | |
| Immediately post-MCAo | None | None | None | Severe |
| After perfusion re-established | None | None | None | Moderate |

What is claimed is:

1. An oligosaccharide-biopolymer compound having a formula

B'-(A-B)$_n$-A'-L-Y-Biopolymer wherein

B'-(A-B)$_n$-A'- is an oligosaccharide moiety wherein

A and B are sugars forming a repeating disaccharide unit in which A and B are joined covalently by a glycosidic bond between C-1 of sugar A and C-3 or C-4 of sugar B, and the repeating disaccharide units are joined covalently to form an oligosaccharide by a glycosidic bond between C-1 of sugar B of a first disaccharide unit and C-3 or C-4 of sugar A in a next successive disaccharide unit, B' is a sugar at a non-reducing terminus of said oligosaccharide of ring structure identical to sugar B, A' is a 1-amino, 1-amido, or 1-imino acyclic hexose joined covalently by a glycosidic bond between C-1 of sugar B at a terminus opposite the non-reducing terminus of said oligosaccharide and C-3 or C-4 of sugar A', and n is an integer from 2 to 20;

L is an aliphatic, acyclic carbon chain which links Y to the 1-amino, 1-amido or 1-imino group attached to C-1 of sugar A', the aliphatic, acyclic carbon chain containing one or more moieties selected from the group consisting of ether, thio ether, and amide; and Y is selected from the group consisting of a methylene radical, β-hydroxyethylene radical, carboxyl radical, succinamide alpha radical, and a covalent bond.

2. The compound of claim 1, wherein said sugars A and B are selected from the group consisting of N-acetylgalactosamine, N-acetylglucosamine, glucuronic acid, iduronic acid, and glucose.

3. The compound of claim 1, wherein said oligosaccharide is an acid hydrolyzed polysaccharide selected from the group consisting of chondroitin-4-sulfate, chondroitin-6-sulfate, and hyaluronic acid in a molecular size range of 1000–15000 daltons.

4. The compound of claim 1 wherein said biopolymer is selected from the group consisting of a protein, a polysaccharide, and a polynucleotide.

5. An oligosaccharide-biopolymer compound having a formula

B'-(A-B)$_n$-A'-L-Y-Biopolymer wherein

B'-(A-B)$_n$-A'- is an oligosaccharide moiety wherein

A and B are sugars forming a repeating disaccharide unit in which A and B are joined covalently by a glycosidic bond between C-1 of sugar A and C-3 or C-4 of sugar B, and the repeating disaccharide units are joined covalently to form an oligosaccharide by a glycosidic bond between C-1 of sugar B of a first disaccharide unit and C-3 or C-4 of sugar A in a next successive disaccharide unit, B' is a sugar at a non-reducing terminus of said oligosaccharide of ring structure identical to sugar B, A' is a 1-amino, 1-amido, or 1-imino acyclic hexose joined covalently by a glycosidic bond between C-1 of sugar B at a terminus opposite the non-reducing terminus of said oligosaccharide and C-3 or C-4 of sugar A', and n is an integer from 2 to 20;

L is an aliphatic, acyclic carbon chain which links Y to the 1-amino, 1-amido or 1-imino group attached to C-1 of sugar A', the aliphatic, acyclic carbon chain containing one or more moieties selected from the group consisting of ether, thio ether, and amide; and Y is selected from the group consisting of a methylene radical, β-hydroxyethylene radical, carboxyl radical, succinamide alpha radical, and a covalent bond; and the biopolymer is a chemically-modified hemoglobin.

6. The compound of claim 5 wherein said sugars A and B are selected from the group consisting of N-acetylgalactosamine, N-acetylglucosamine, glucuronic acid, iduronic acid, and glucose.

7. The compound of claim 5 wherein said oligosaccharide is an acid hydrolyzed polysaccharide selected from the group consisting of chondroitin-4-sulfate, chondroitin-6-sulfate, and hyaluronic acid in a molecular size range of 1,000 to 15,000 daltons.

8. The compound of claim 5 wherein said biopolymer is a crosslinked hemoglobin.

9. The compound of claim 8 wherein said crosslinked hemoglobin is a diaspirin crosslinked human hemoglobin.

* * * * *